United States Patent [19]

Croset et al.

[11] 4,271,000
[45] Jun. 2, 1981

[54] ELECTROCHEMICAL SENSOR FOR MEASURING RELATIVE CONCENTRATIONS OF REACTIVE SPECIES IN A FLUID MIXTURE

[75] Inventors: Michel Croset; Gonzalo Velasco, both of Paris, France

[73] Assignee: Thomson-CSF, Paris, France

[21] Appl. No.: 91,757

[22] Filed: Nov. 6, 1979

[30] Foreign Application Priority Data

Nov. 7, 1978 [FR] France .................. 78 31438

[51] Int. Cl.³ .............................. G01N 27/58
[52] U.S. Cl. .................................. 204/195 S
[58] Field of Search ................. 204/195 S, 1 S; 123/32 EE, 119 EC, 119 E; 60/276

[56] References Cited

U.S. PATENT DOCUMENTS

| | | | |
|---|---|---|---|
| 3,597,345 | 8/1971 | Hickam et al. | 204/195 S |
| 3,978,006 | 8/1976 | Topp et al. | 204/195 S X |
| 4,158,166 | 6/1979 | Isenberg | 204/195 S X |

Primary Examiner—G. L. Kaplan
Attorney, Agent, or Firm—Cushman, Darby & Cushman

[57] ABSTRACT

The sensor comprises an electrochemical measuring cell having a flat structure and constituted by two electrodes in contact with a solid electrolyte. One electrode which is formed of catalytic material has an extension of predetermined length in at least one direction parallel to the plane of the cell in order to be placed in contact with the fluid mixture and to bring it into thermodynamic equilibrium prior to analysis.

9 Claims, 12 Drawing Figures

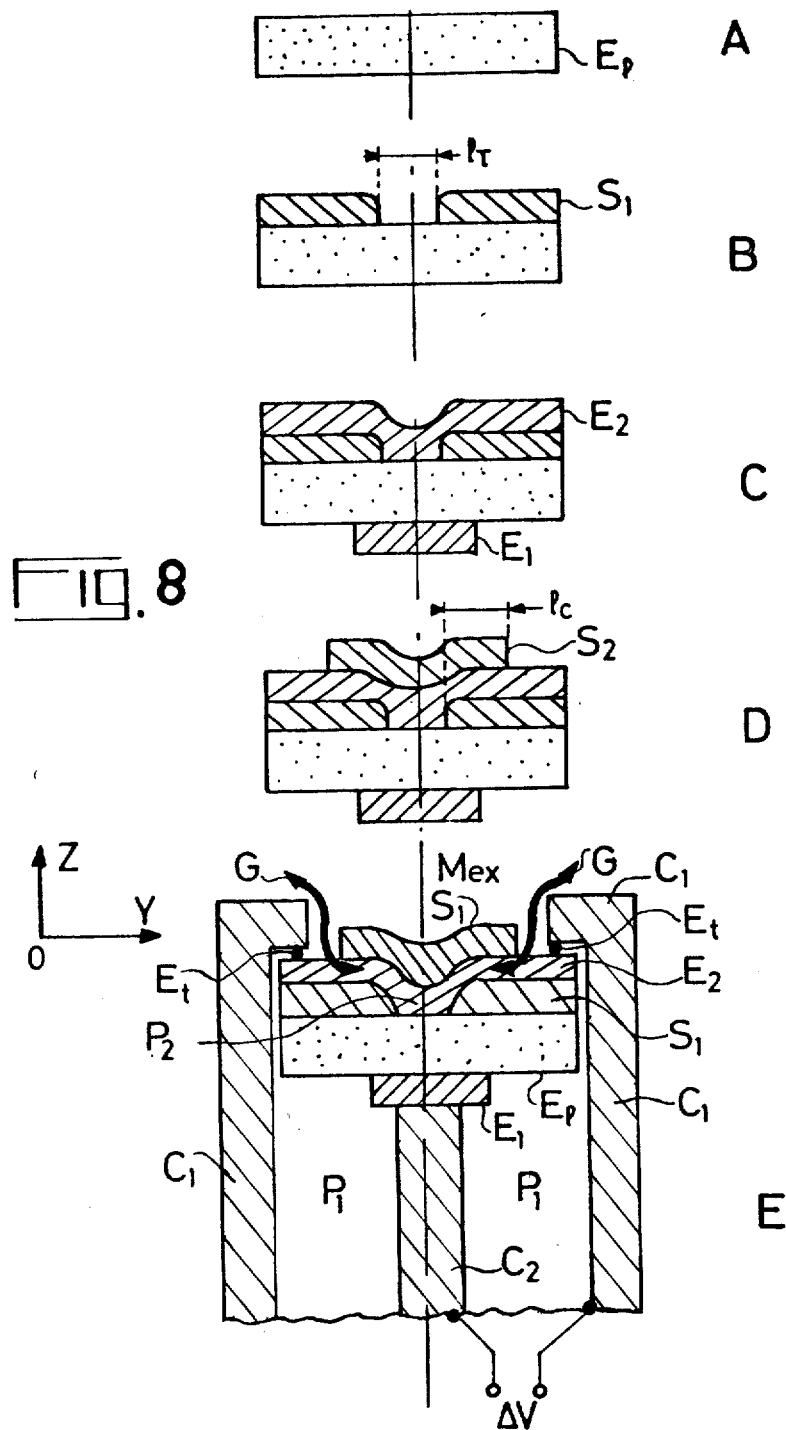

ELECTROCHEMICAL SENSOR FOR MEASURING RELATIVE CONCENTRATIONS OF REACTIVE SPECIES IN A FLUID MIXTURE

This invention relates to electrochemical sensors for measuring relative concentrations of reactive species in a fluid mixture. The invention relates in particular to a sensor for measuring the partial pressure of one of the species contained in a gas.

One of the well-known families of sensors for the measurement of partial gas pressures operates on the principle of the concentration cell. The gaseous medium to be analyzed is separated from a reference medium by a wall of solid electrolyte, each face of which carries an electrode. The solid electrolyte $E_l$ is an exclusive ionic conductor of the species to be analyzed or of an ion which is capable of reacting with this species. The electrodes $E_1$, $E_2$ deliver or collect the electrons required for the electrochemical reactions which take place at the interfaces.

The basic operating principle of a sensor for measuring the partial pressure of oxygen is illustrated in FIG. 1. The partial pressure of oxygen $P_1$ of the compartment 1 is known and serves as a reference. The following reactions take place on the two electrodes $E_1$, $E_2$ (of platinum, for example):

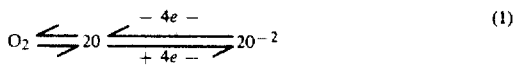
(1)

In the state of equilibrium which corresponds to equalization of the electrochemical potential of the oxygen within the three media, the voltage $\Delta V$ developed across the terminals of the electrodes is given by the Nernst law:

$$\Delta V = \frac{RT}{4F} LN\left(\frac{P_1}{P_2}\right) \quad (2)$$

where:
R = Ideal gas constant = 8.314 J/(mole.°K)
F = Faraday number = 96490
T = Absolute temperature in degrees Kelvin
$P_1$ and $P_2$ = Partial pressures of media 1 and 2.

The value $P_2$ is deduced from a knowledge of $P_1$ (reference) and from a measurement of $\Delta V$ and T.

In this mode of operation in which the gas of compartment 2 is in thermodynamic equilibrium, the function of the electrode is limited to the catalysis of the oxidation-reduction reaction:

$$X_n + n\, ae^- \rightleftharpoons nX^{a-} \quad (3)$$

The electrolyte can be lime-stabilized zirconia.

Sensors of this type can also be employed for analysis of the partial pressure of one of the constituents of a gas mixture in a state of thermodynamic disequilibrium. Two requirements corresponding to two different modes of operation of the sensor may accordingly arise:

either the sensor measures the true partial pressure of the constituent to be analyzed in its state of disequilibrium; in this case, the electrode must not modify the composition to any appreciable extent or in other words must not catalyze the chemical reaction between the constituent to be analyzed and the other constituents of the mixture or must do so only to a slight extent. Referring to FIG. 1, this means that if the compartment 2 contains a mixture of oxygen $O_2$ and of carbon monoxide CO, the reaction: $2+CO\ O_2 \rightleftharpoons 2\ CO_2$ must be prevented. The electrode must only take part in the equilibration of the electrochemical potential of either of the two constituents, namely oxygen or carbon monoxide;

or alternatively, the sensor measures the partial pressure which the detected species would have if the gas mixture has attained thermodynamic equilibrium.

It may accordingly be stated with reference to the example given in the foregoing that, at least at the level of the measurement or in other words at the level of the electrode/solid electrolyte interface, the combustion reaction is complete until the reversible thermodynamic equilibrium is attained:

$$2CO + O_2 \rightleftharpoons 2CO_2 \quad (4)$$

with

(5)

where K(T) is a temperature-dependent coefficient of equilibrium.

The measured oxygen or carbon monoxide accordingly corresponds to the excess quantity of one of these two constituents defined by equation (4), and $|CO|$, $|O^2|^{\frac{1}{2}}$ and $|CO^2|$ are the partial pressures respectively of carbon monoxide, oxygen and carbon dioxide gas.

An operation of this type is particularly advantageous for defining the difference with respect to the stoichiometry of a mixture.

Certain solutions were proposed in the prior art approach to this problem and all were based on the concept of a "test sample". In point of fact, it serves no useful purpose and is sometimes harmful, difficult or costly to bring the entire quantity of gas to the stage of thermodynamic equilibrium; it is easier to establish this equilibrium on only a small fraction of this gas which is replenished at the desired rate in order to tend towards continuous analysis. The solutions consist in limiting gas exchange between the medium to be analyzed and the electrode which is chosen on account of its high catalytic activity. Two typical arrangements can be mentioned among others and are shown diagrammatically in FIGS. 2 and 3. In FIG. 2, the sensor is placed within an enclosure which communicates with the external medium Mex through an orifice Tr of predetermined size. Exchanges of gas G between the enclosure and the external medium are carried out by gaseous diffusion; this process can be assisted by modifications in total pressure of the external medium.

The catalytic activity of the electrode $E_2$ must be sufficient to ensure that thermodynamic equilibrium is rapidly attained within the enclosure (medium $P_2$), taking into account the gas exchange kinetics between enclosure and external medium Mex. Should this not be the case, the thickness of the electrode $E_2$ through which the gases diffuse towards the interface between electrode and solid electrolyte $E_l$ must be chosen so as to ensure that the reaction proceeds to completion during this diffusion until thermodynamic equilibrium is attained at the level of the interface. FIG. 3 shows another approach on the same principle: the electrode is covered with a permeable substance $P_2$ which limits the gas flow towards this electrode. In both cases, the voltage developed between the electrodes $E_1$ and $E_2$ is measured. The medium $P_1$ is the reference medium.

In all these solutions, the electrode $E_2$ is supplied with gas in the direction of its thickness. The underlying principle of this mode of operation is shown diagrammatically in more detailed form in FIG. 4, in which the one-dimensional geometry is clearly apparent; in fact, the coordinate Z is the only parameter employed in the operation since the situation at each point of the plane X-Y is equivalent in respect of a given value of the Z-axis. The surface of the electrode $E_2$ is supplied with a gas mixture through an impedance represented diagrammatically in FIG. 4 by a plate P which is pierced with a hole Tr. When in contact with this surface, the gas is not usually in thermodynamic equilibrium. Equilibrium must be attained during traversal of the electrode $E_2$ in the direction of the Z-axis by virtue of the catalytic activity of this latter. The two parameters governing the catalytic power of the system are therefore the values of the impedance Tr and of the thickness $\Delta Z$ of the electrode.

The major disadvantages of this geometry are the following:

the cost price of the electrode (which is usually made of precious metal) is proportional to its thickness;

the difficulty involved in obtaining total catalysis before reaching the electrode-electrolyte interface, with the result that rival species having different exchange activation energies are permitted to reach said interface and cause temperature drifts in the response of the sensor.

In order to overcome these defects, the invention proposes sensor structures in which the catalytic process is dissociated from the partial-pressure measurement proper. To this end, the gas to be analyzed must flow along a path of predetermined length within an enclosure located upstream of the measuring cell, namely the cell $E_2$-$E_r$-$E_1$ as described in the foregoing. The traversal no longer takes place along the Z-axis as indicated in FIG. 4 but in any favorable direction and especially in a direction parallel to the X-Y plane. The gas is therefore directed at least along one of the coordinate axes other than the Z-axis and passes either close to a catalysis surface or within the catalyst, said catalyst being constituted by the extension of one of the measuring electrodes (along the coordinate axis or axes other than the Z-axis). In these two approaches, it is not necessary to make provision for a catalyst of substantial thickness. In addition to the economy thus achieved, it is an advantage to adopt the thin-film or thick-film deposition techniques which are frequently employed in the microelectronics industry.

The excess or insufficiency of one of the constituent species of the gas is therefore measured since this measurement is carried out upstream of the catalyst on a gas which is in thermodynamic equilibrium.

This mode of operation is particularly advantageous for analyzing the composition of the burned gases at the outlet of an internal combustion engine or of the burner of a boiler, for example. There is employed in this case a measuring cell in which the electrolyte is an ionic conductor of oxygen such as lime-stabilized zirconia, for example. It is in fact known that the exhaust gases of an automotive vehicle contain carbon dioxide gas $CO_2$, carbon monoxide CO and oxygen $O_2$ among other constituents.

In order to maintain a pre-established engine speed or in order to satisfy anti-pollution standards, it is necessary to regulate the air-fuel mixture, for example. One of the known means for the achievement of this regulation is to place in a feedback loop a sensor for analyzing the partial pressure of oxygen contained in the exhaust gases.

The structure of sensors in accordance with the invention which measures only the difference with respect to stoichiometry is therefore particularly advantageous in an application of this type.

The invention is consequently directed to an electrochemical sensor for measuring relative concentrations of reactive species contained in a fluid mixture. The sensor comprises an electrochemical cell having a flat structure which is sensitive to an excess quantity of one of the reactive species with respect to stoichiometry of the reaction and an enclosure which communicates with the fluid mixture to be analyzed through a first orifice and with said electrochemical cell through a second orifice. Said cell comprises a first electrode in contact with said enclosure, a second electrode isolated from said enclosure and in contact with a reference medium, and a solid electrolyte which is an ionic conductor for the species to be analyzed or for an ion which is capable of reacting with said species, said electrolyte being in contact with said two electrodes of the electrochemical cell. Said enclosure is designed in the form of a duct which is parallel along its greatest dimension to the plane of said first electrode of the electrochemical cell, said first electrode being formed of catalytic material and deposited on the bottom wall of the enclosure. Furthermore, said first electrode is divided into two zones. The first zone constitutes with said second electrode and said solid electrolyte of the electrochemical cell a measurement zone which is sensitive to the species to be analyzed. The second zone extends over a predetermined distance of said duct in the direction of the aforesaid orifice for providing a communication with said fluid mixture to be analyzed and constitutes a zone for catalysis of said mixture.

A more complete understanding of the invention will be gained from the following description in which further advantages will become apparent, reference being made to the accompanying drawings, in which:

FIGS. 7 to 9 are examples of construction of sensors in a second approach according to the invention;

In the following description, examples of construction of sensors according to the invention will be explained in the case of a practical application which consists in measuring the composition of the exhaust gas of an internal combustion engine. This will involve the use of a measuring cell with electrodes of platinum and an electrolyte of lime-stabilized zirconia. It will be understood, however, that this choice does not imply any limitation of the scope of the invention. Different measuring cells can be employed and, among other nonlimitative examples, silica can be used as electrolyte for measuring the partial pressure of hydrogen and lanthanum can serve to measure the partial pressure of fluorine.

Moreover, the following conventions and abbreviations will be employed in connection with the description of the accompanying figures:

External medium: Mex
Ambiet air or atmosphere: AAb
Gas to be analyzed: G
Electrolyte: $E_l$
Catalyst: $C_t$
Partial pressure of the reference medium: $P_1$
Partial pressure of the gas to be analyzed at the level of the measuring electrode $E_2$: $P_2$
Electrically insulating and leak-tight materials: $S_1$, $S_2$
Seals providing leak-tightness and electrical contact: $E_t$
Potential difference between the measuring electrodes: $\Delta V$
Calibrated orifice for limiting gaseous exchange with the external medium: $T_r$.

Figure 1:
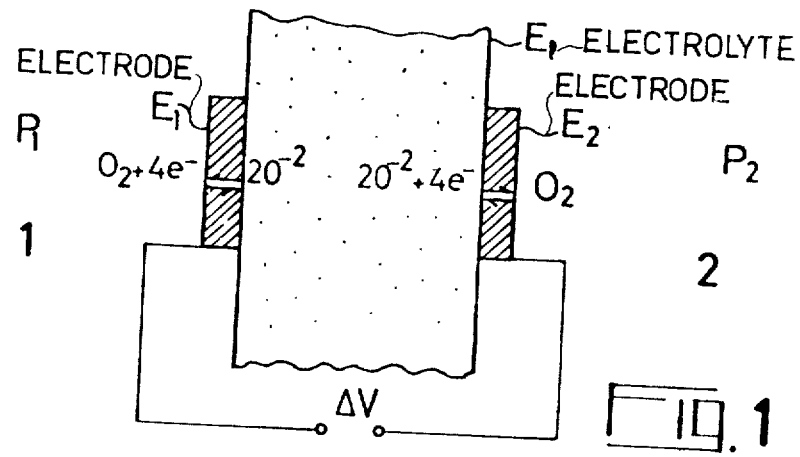
FIG. 1 illustrates the operation of the measuring cell employed in the electrochemical concentration sensors.
Figure 2:
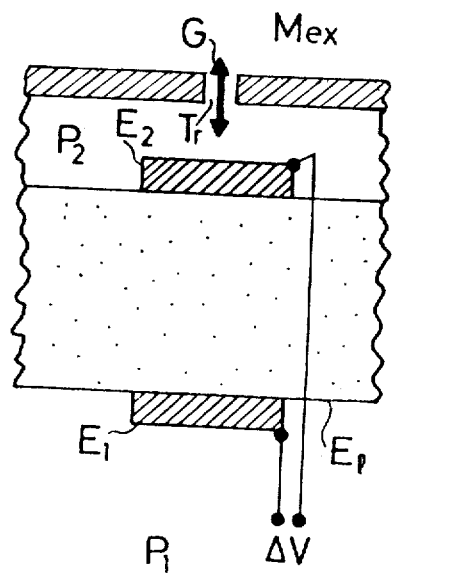
FIGS. 2 and 3 are general arrangement diagrams of two sensors of the prior art.
Figure 3:
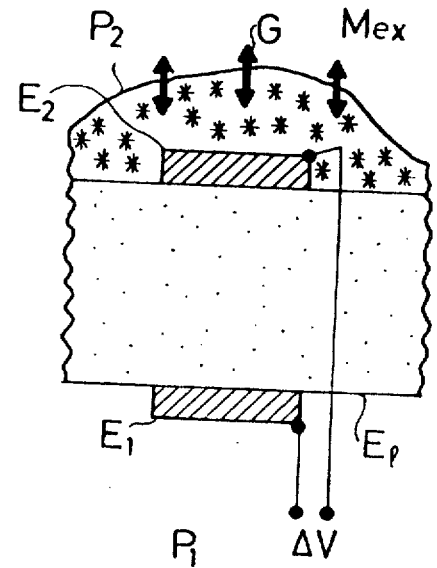
Figure 4:
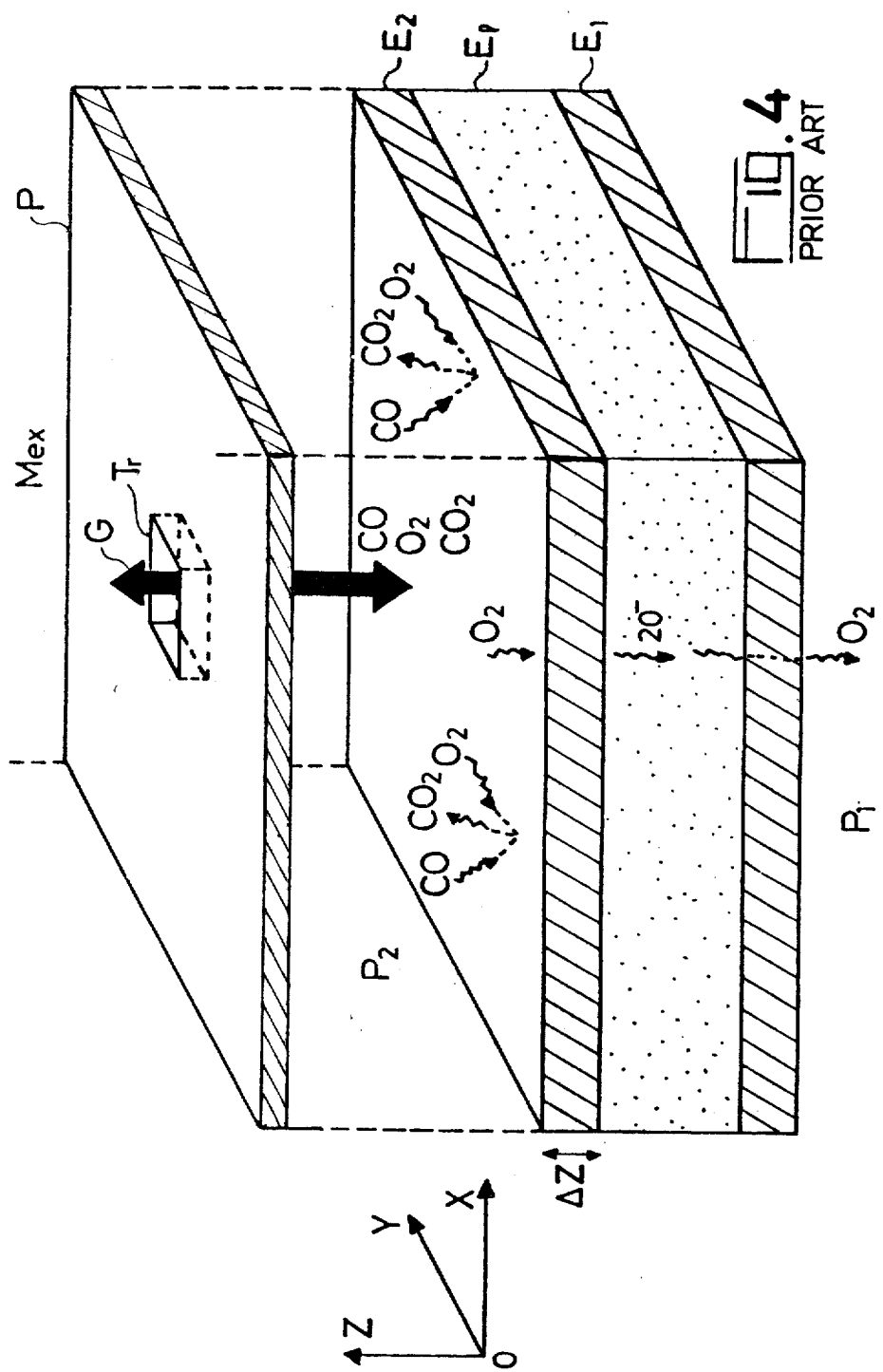
FIG. 4 is a more detailed general arrangement diagram illustrating the operation of a sensor of the prior art.
Figure 5:
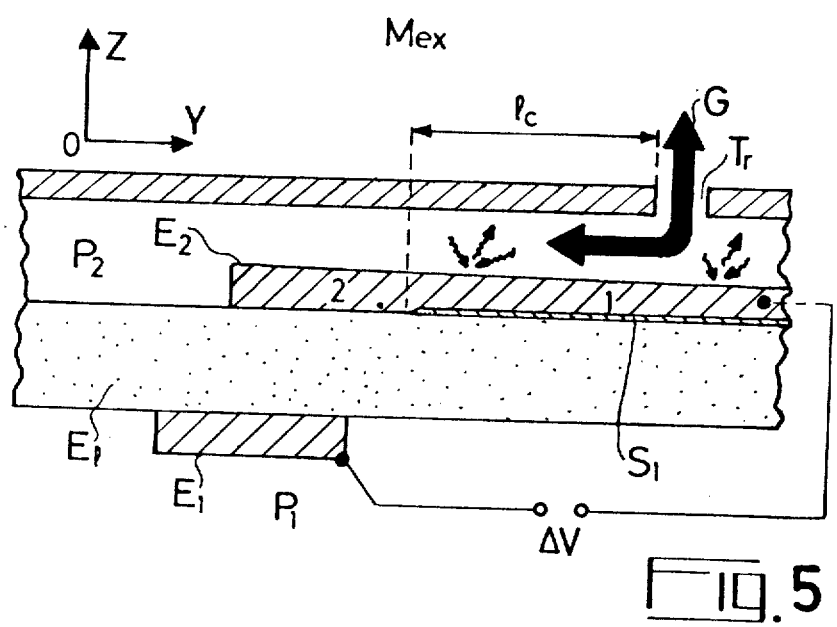
FIG. 5 is an example of construction of a sensor in a first approach according to the invention.

FIG. 5 illustrates a first example of construction of a sensor in accordance with a first approach contemplated by the invention. The gas to be analyzed penetrates through an orifice $T_r$ into the measuring sensor of elongated shape, then flows through an enclosure over a distance $l_c$. The wall of said enclosure is covered with a thin film of catalyst $C_t$ constituted by the extension of one of the electrodes ($E_2$) of the measuring cell, namely the cell $E_2$-$E_l$-$E_1$ as described in the foregoing. The electrode $E_2$ is therefore the electrode which is in contact with the gas to be analyzed. The flow path of the gas G over the distance $l_c$ has been of sufficient length to ensure that the gas has attained thermodynamic equilibrium under the influence of the catalyst. The electrode $E_1$ is in contact with the reference medium $P_1$ which can be ambient air. Two zones can be distinguished: in zone 1, the electrode $E_2$ is separated from the solid electrolyte $E_l$ by a layer of inert insulating material $S_1$ formed by deposition of an insulating film at the surface of said electrolyte. In an alternative form of construction (not shown in the drawings), the solid electrolyte $E_l$ can be replaced in this zone by said insulating material $S_1$ which can accordingly constitute the support of zone 1 of the electrode $E_2$. In this zone, the electrode serves as a catalyst and catalyzes the chemical reaction of the gases in the nonequilibrium state which penetrate through the orifice $T_r$. In zone 2, the electrode $E_2$ is in contact with the solid electrolyte $E_l$; its catalytic action along the coordinate axis Z is no longer fundamental insofar as the gases have attained thermodynamic equilibrium after passing through a distance corresponding to the length $l_c$ of the zone 1 and the thickness of said electrode can be reduced to a minimum. Zone 2 serves as an electrode for measuring potential in conjunction with the other components of the cell $E_1$-$E_l$-$E_2$. The only parameter to be adjusted is $l_c$, namely the distance over which catalysis takes place. This parameter is dependent on the size of the orifice $T_r$ which serves to carry out gas exchange with the external medium, performs the function of an impedance with respect to the gas G to be analyzed and limits exchanges with the external medium Mex. The measurement proper is carried out by connecting the electrodes $E_1$ and $E_2$ to a suitable electric measuring system (not shown in the drawings). The order of magnitude of the potential difference developed between these two electrodes $\Delta V$ is of the order of a few hundred millivolts. The measuring system must provide a high value of input impedance in order to limit the current which flows through the cell and consequently in order to limit the potential drop arising from the internal resistance of the cell. There will be given hereinafter a few examples of response curves: potential difference as a function of the difference in partial pressure of a species which is present in the media $P_1$ and $P_2$. As mentioned earlier, the reference medium $P_1$ can be ambient air but can also be any other suitable gas contained in a reservoir, for example. This aspect does not come within the scope of the invention.

Figure 6:
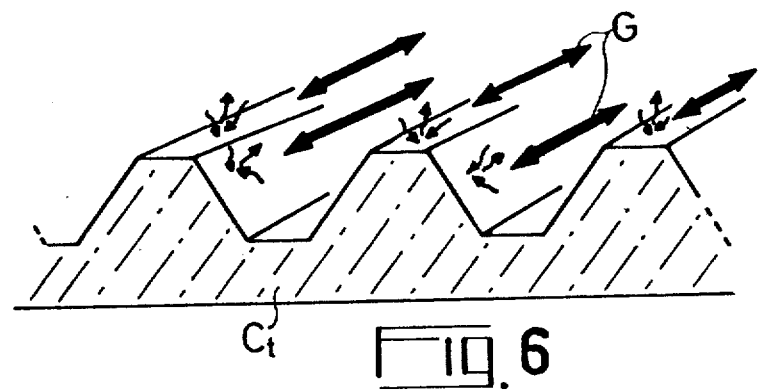
FIG. 6 illustrates a technological improvement which is applicable to the sensor of FIG. 5.

FIG. 6 introduces a further improvement which is applicable to the sensor of FIG. 5. It is in fact important to ensure that the contact surface between gas and catalyst is as extensible as possible. The catalytic deposit can be given a structure which serves to increase this contact surface. FIG. 6 illustrates one example of a corrugated structure which meets this criterion. The arrows G show the direction of flow of the gas along the furrows of the catalyst $C_t$. This example does not imply any limitation, however. It is thus possible to employ all types of surface structures which are compatible with thin-film deposition, namely grooves, surface excrescences and so forth. This improvement achieves enhanced efficiency of the catalyst.

In the sensor structure described in the foregoing, catalysis takes place in a "gas chamber". A cavity must accordingly be provided within the sensor and gives rise to difficulties of a technological order. These difficulties can be overcome by adopting structures which permit catalysis by diffusion through a solid and which will be described hereinafter.

Figure 7:
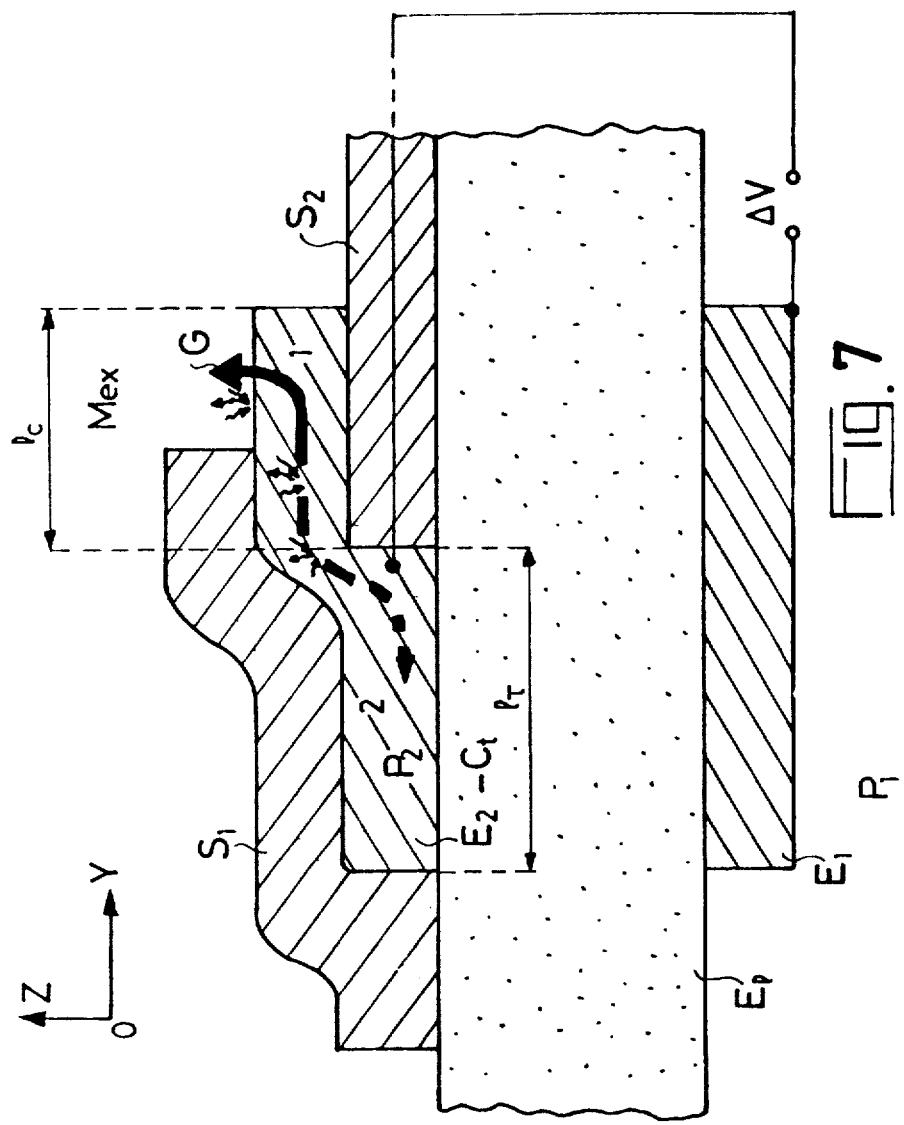

FIG. 7 presents the case in which catalysis is performed not by contact with a catalyst deposited at the surface but by passage through a porous or permeable catalytic substance or at least a substance which is charged with catalyst. This constitutes a first example of construction in accordance with a second approach contemplated by the invention. In this approach, catalysis takes place by diffusion in a solid medium. In this case the catalytic substance $C_t$ also performs the function of an impedance with respect to exchanges with the external medium and there is no longer any need to have recourse to a calibrated orifice ($T_r$ in FIG. 5) in order to limit exchanges between the external medium and the measuring cell. It is accordingly necessary to prevent any direct contact (along the coordinate axis Z) between the external medium Mex and that portion of the electrode $E_2$ which is combined with the catalyst and is in contact with the solid electrolyte $E_l$. This is achieved by means of an insulating layer $S_1$ (of material which does not exhibit ionic or electronic conductivity). Catalysis of the reactive gases takes place in the zone 1 of the electrode $E_2$ over a distance $l_c$ and said gases attain thermodynamic equilibrium either before or in contact with the zone 2, or measuring zone of the electrode $E_2$. In consequence, only that species which is in excess with respect to stoichiometry, namely oxygen or carbon monoxide in the example under consideration, reaches the active interface between electrode $E_2$ and electrolyte $E_l$.

FIG. 7 shows the two parameters to be adjusted: first of all the length $l_c$, or distance of catalysis, which is dependent on the geometry and on the nature of the electrode $E_2$ in the zone 1 and on the nature of the reactive gases. This value must be sufficient to ensure complete catalysis. However, an excessive length with respect to this optimum value will increase the response time of the sensor to no useful purpose and will reduce its performances in dynamic operation. The second parameter $l_r$, defines the value of the electrical capacitance of the electrode-electrolyte interface. A value of $l_r$ which is too high is also liable to impair the response time of the sensor. As in the previous instance, the electrodes $E_1$, $E_2$ are connected to a measuring system (not shown in the figure).

As in the previous case, the reference medium $P_1$ can be ambient air or any other suitable gas. The medium $P_2$ which represents the partial pressure of the species in excess or in insufficient quantity with respect to stoichiometry (oxygen, for example) is constituted by the internal space occupied by the electrode $E_2$ within the zone 2 having a length $l_r$. The catalysis enclosure is constituted by the internal space occupied by the electrode $E_2$ within the zone 1 having a length $l_c$.

Figure 9:
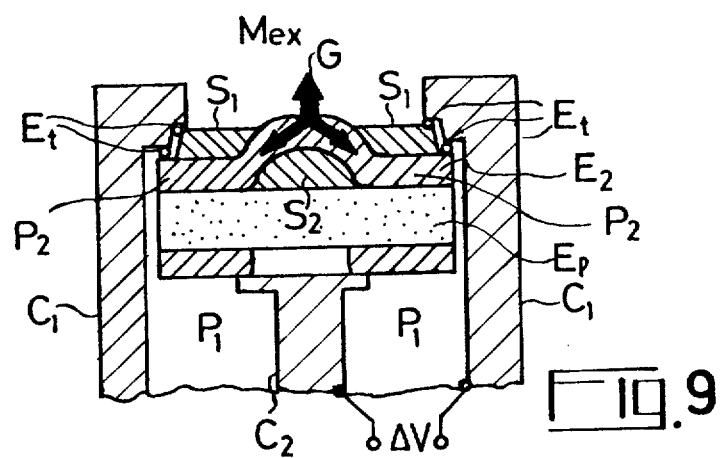

Two further examples of construction in accordance with the second approach are illustrated in FIGS. 8 and 9.

FIG. 8 also illustrates in greater detail the different stages A to E involved in the fabrication of the sensor. In these two examples, the sensor is essentially designed in the form of a pastille comprising a stack of discs constituted by the different components.

The basic element (stage A) is a ceramic pastille of lime-stabilized zirconia (12% doping). This pastille is fabricated in the form of a disc having a diameter of 5 mm and a thickness of 1 mm. This disc constitutes the electrolyte $E_t$. One face is covered annularly by an enamel insulator $S_1$ having high temperature strength (stage B) which defines an uncovered central space having a diameter $l_r$. This insulator is of the type employed in the technology of hybrid circuits which are well known to those versed in the art. A deposit of platinum (stage C) 0.1 to a few tens of microns in thickness is then formed at the front face over the entire surface and at the rear face at the center of the disc. These deposits form the electrodes $E_2$ and $E_1$. Deposition can be performed by screen process, with a brush or by any other technique (vacuum deposition, for example). The second insulating layer $S_2$ is then deposited at the center of the front face (stage D), with the result that said second insulator projects beyond the first annular deposit to a distance $l_c$; the covered portion $l_c$ of the electrode $E_2$ constitutes the catalysis enclosure. The center of the pastille is then applied against the bottom of a metallic tube (stage E) which is in electrical contact $C_1$ with the platinum of the front face. The electrical contact $C_2$ with the rear face is produced under the action of pressure. A seal $E_t$ of electrically conductive material is placed between the electrode $E_2$ and the tube $C_1$. During operation, the interior of the tube $C_1$ is in contact with a reference medium $P_1$ such as the atmosphere, for example, and the front face is immersed in the gas G to be analyzed. For the practical operation of a sensor of this type between 400° C. and 1000° C., typical values of $l_r$ and $l_c$ are as follows:

$l_r$: 0.1 mm to 2 mm $l_c$: 0.1 mm to 0.5 mm when the electrode is deposited by screen process to a thickness of 1 μm.

The electrolyte $E_t$ can be constituted by a disc having a diameter of approximately 0.5 mm (and a thickness of 1 mm as already mentioned).

FIG. 9 will now be described briefly and shows a structure which is similar to that of FIG. 8. The constituent elements have positions which are essentially complementary to those of FIG. 8. In particular, the measuring electrodes $E_2$ and $E_1$ are constituted by a ring and the gas inlet orifice will on the contrary be centered. There are again shown in addition the elements which have already been described with reference to FIG. 8, namely $S_1$, $S_2$, $E_t$, $C_1$, $C_2$, $E_t$.

The operation of the sensors of FIGS. 8 and 9 is identical with the operation of FIG. 7. The catalysis enclosure shown in FIG. 7 has an essentially linear configuration (that is to say along one coordinate, namely the Y-axis). The catalysis enclosure of FIGS. 8 and 9 has a configuration of revolution in a plane at right angles to the Z-axis. Construction of sensors in accordance with the invention is not limited to these configurations, however. In particular, the pastilles shown in FIGS. 8 and 9 can be of either square or rectangular shape. In all cases, said pastilles can readily be fabricated by means of ceramic techniques and consequently be highly compact.

Similarly, in the construction of a measuring cell of the concentration cell type, electrolytes other than the type mentioned may be employed. It is possible in particular to make use of thoria or of cerium oxide which are stabilized by elements such as calcium, yttrium or scandium and so forth, that is to say one or a number of elements of columns $II_A$ and $III_B$ of the periodic table. In addition to platinum, the electrodes can be for example of gold or silver or of an alloy based on these metals.

The catalyst can be of platinum having either a compact or a porous texture. It can also be constituted by an inert porous substance such as, for example, alumina or zirconia charged with platinum or metal oxides such as: $ZnO$, $CeO_2$, $MnO_2$, $Mn_2O$, $Fe_2O_3$, $CO_2O_3$, $NiO$, $CuO$, $Cu_2O$, $Cr_2O_3$, $TiO_2$, $V_2O_5$, $Ag_2O$ or $PbO$. To those versed in the art, all these oxides are known to have catalytic properties.

Figure 10:
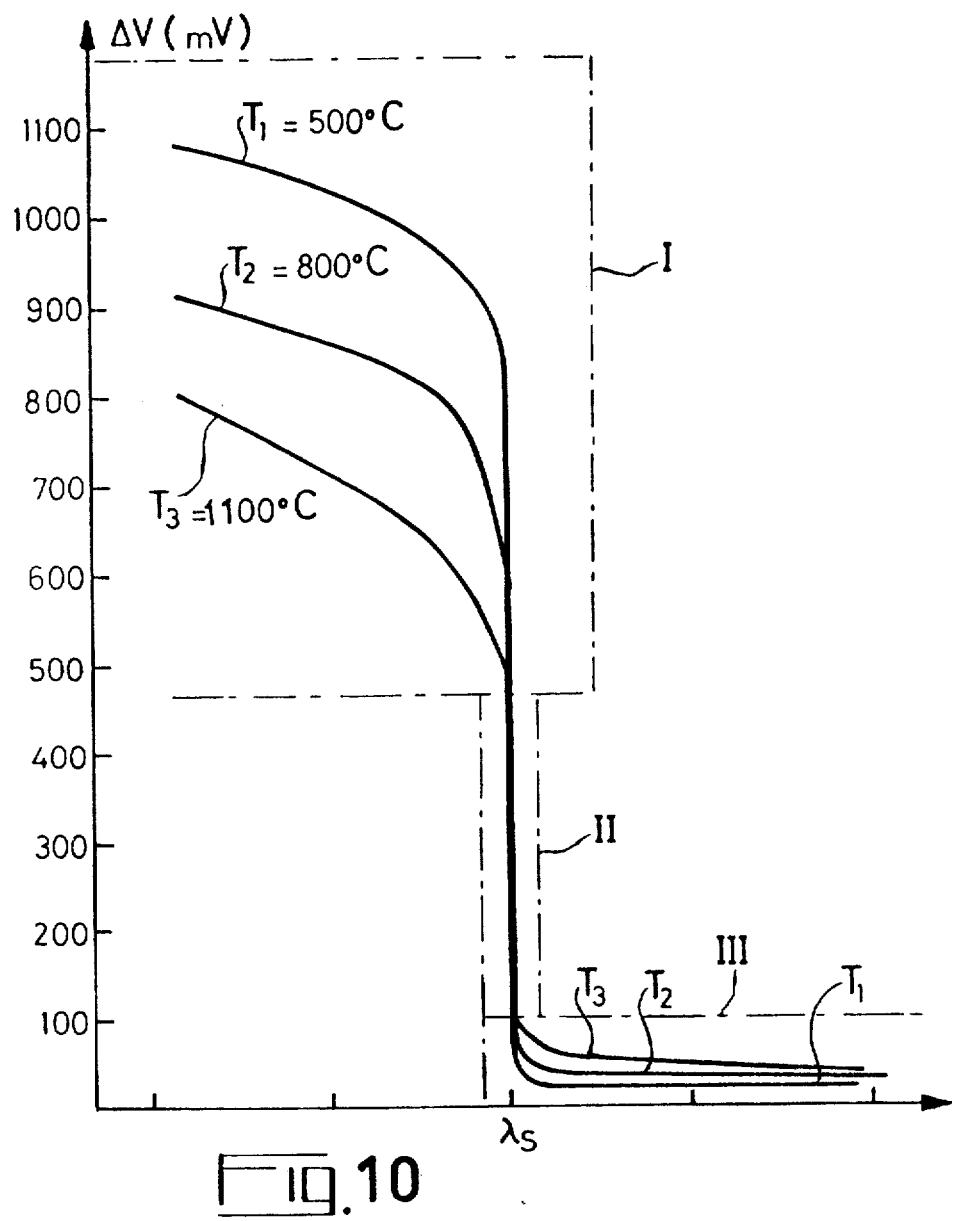
FIG. 10 is a set of response curves of sensors according to the invention.
Figure 11:
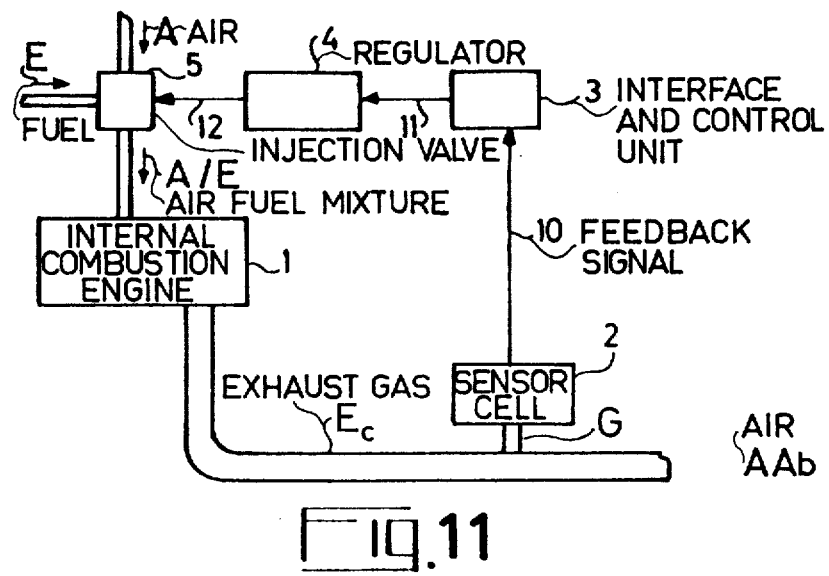
FIG. 11 shows one example of application of sensors according to the invention.
Figure 12:
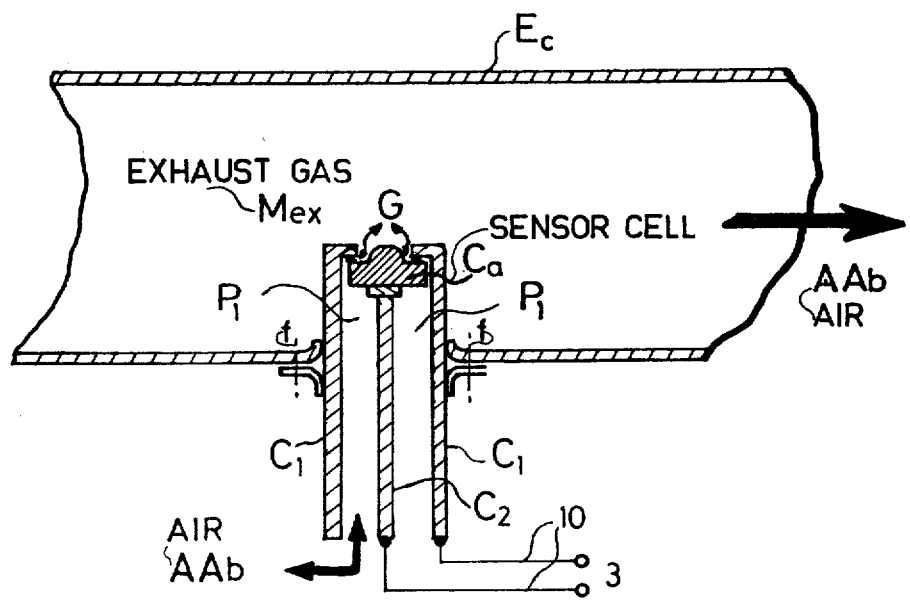
FIG. 12 is a sectional view illustrating a detail of FIG. 11.

Referring now to FIGS. 10 to 12, there will be described a preferred example of application of sensors constructed in accordance with the invention.

FIG. 10 illustrates a set of response curves of sensors for measuring the concentration of oxygen in the exhaust gases of an internal combustion engine. Each curve represents the potential difference as a function of the concentration of oxygen in the exhaust gases at constant temperature. Three zones will be observed: in zones I and III, the different curves are sharply differentiated from each other. In fact, if reference is made to relations (1) and (5) indicated earlier, it is noted that these relations both contain the "absolute temperature T" parameter. It is therefore difficult to utilize these portions of curves since the exhaust gases do not have a constant temperature. On the other hand, in zone II of FIG. 12 which corresponds to inflexion, the different curves practically coincide. In consequence, the output of the sensor is transmitted to an electric control unit which detects rapid inflexion of the curve $\Delta V$ about the point of abscissa $\lambda_s$ which represents the stoichiometric ratio of the mixture as measured at the level of the electrode $E_2$.

FIG. 11 is a block diagram showing the regulation of the air-fuel mixture in an internal combustion engine 1. The engine 1 comprises an air intake A and a fuel intake E, said air and fuel being mixed within a unit 5. Said unit can be a carburetor of the float-chamber type, an injection device or any other similar device. The mixture is fed to the engine 1 through the duct A/E. The unit 5 is under the control of a regulating unit 4. The connection 12 can be a mechanical coupling shaft, for example. The burned gases are then discharged into the atmosphere AAb through an exhaust pipe $E_c$. A sensor 2 in accordance with the invention is placed in the flow path and communicates with the exhaust gas through the duct designated by the reference G. In practice, the sensor is inserted in the exhaust pipe and maintained in position by any suitable fastening means f, as illustrated in FIG. 12. The duct G is limited to a calibrated orifice T in the case of the sensor shown in FIG. 5 or to the orifice which is left free within the insulator in the case of the sensors shown in FIGS. 7 to 9.

The sensor illustrated in FIG. 12 is of the same type as the sensor of FIG. 8. There are again shown the contacts $C_1$, $C_2$, the outlet G which provides an exchange with the external medium Mex, and the pastille $C_a$ constitutes by a stack of different layers as described with reference to FIG. 8. The electrical signal developed between the electrodes $E_2$ and $E_1$ of the measuring cell is transmitted to a control unit by means of the electrical connections 10 via the contacts $C_1$ and $C_2$. As mentioned earlier, the control unit must have a high input impedance. By making use of a threshold logic circuit, for example, said control unit must be capable of detecting the inflexion of the curve $\Delta V$ about $\lambda_s$ and the output of said unit controls the regulator 4 via the connection 11. In the case under consideration, the reference medium $P_1$ is ambient air AAb.

This method of regulation is well known in the field of automobile electronics. It is particularly advantageous, however, to employ a sensor according to the invention in which the gas to be analyzed is brought into thermodynamic equilibrium before reaching the measuring zone of the electrode $E_2$.

Furthermore, this method is not limited to regulation of the air-fuel mixture of an internal combustion engine. By way of example without any limitation being implied and without introducing any change in the structure shown in the diagram of FIG. 11, the engine 1 can be replaced by the burners of a boiler. In this case the sensor 2 is placed in the burned-gas exhaust system $E_c$.

Finally, although a mixture of gases to be analyzed of the oxygen-carbon monoxide-carbon dioxide type has alone been considered in each embodiment for the sake of enhanced clarity of the description, the use of the sensor is not limited to this analysis alone, as has already been pointed out. It is only necessary to make a suitable choice of solid electrolyte $E_l$ and of the reference medium $P_1$ in order to analyze other gas mixtures or, more generally, other non-ionized fluids.

What is claimed is:

1. An electrochemical sensor for measuring relative concentrations of reactive species contained in a fluid mixture, comprising:
    an electrochemical cell having a flat structure which is sensitive to an excess quantity of one of the reactive species with respect to stoichiometry of the reaction; and
    an enclosure which communicates with the fluid mixture to be analyzed through a first orifice and with said electrochemical cell through a second orifice,
    wherein said cell comprises:
        a first electrode in contact with said enclosure,
        a second electrode isolated from said enclosure and in contact with a reference medium, and
        a solid electrolyte which is an ionic conductor for the species to be analyzed or for an ion which is capable of reacting with said species, said electrolyte being in contact with said two electrodes of the electrochemical cell,
    said enclosure being in the form of a duct which is parallel along its greatest dimension to the plane of said first electrode of the electrochemical cell, and
    wherein said first electrode is formed of catalytic material, said catalytic material being also deposited on the bottom wall of said enclosure,
    said first electrode being also divided into two zones such that the first zone constitutes with said second electrode and said solid electrolyte of the electrochemical cell a measurement zone which is sensitive to the species to be analyzed while the second zone extends over a predetermined distance of said duct in the direction of the aforesaid orifice for providing a communication with said fluid mixture to be analyzed and constitutes a zone for catalysis of said mixture, and
    wherein the surface of the second zone of said first electrode is provided with a corrugated structure in order to increase the surface area in contact with said fluid mixture to be analyzed.

2. A sensor according to claim 1, wherein said electrodes of said electrochemical cell are fabricated by means of the thin-film or thick-film deposition technique.

3. An electrochemical sensor for measuring relative concentrations of reactive species contained in a fluid mixture, comprising:
    an electrochemical cell having a flat structure which is sensitive to an excess quantity of one of the reactive species with respect to stoichiometry of the reaction; and
    an enclosure which communicates with the fluid mixture to be analyzed through a first orifice and with said electrochemical cell through a second orifice,
    wherein said cell comprises:
        a first electrode in contact with said enclosure,
        a second electrode isolated from said enclosure and in contact with a reference medium, and
        a solid electrolyte which is an ionic conductor for the species to be analyzed or for an ion which is capable of reacting with said species, said electrolyte being in contact with said two electrodes of the electrochemical cell,
    said enclosure being in the form of a duct which is parallel along its greatest dimension to the plane of said first electrode of the electrochemical cell, and
    wherein said first electrode is formed of catalytic material, said catalytic material being also deposited on the bottom wall of said enclosure,
    said first electrode being also divided into two zones such that the first zone constitutes with said second electrode and said solid electrolyte of the electrochemical cell a measurement zone which is sensitive to the species to be analyzed while the second zone extends over a predetermined distance of said duct in the directon of the aforesaid orifice for providing a communication with said fluid mixture to be analyzed and constitutes a zone for catalysis of said mixture, and wherein said enclosure is entirely filled with said catalytic material which constitutes said second zone of said first electrode and through which said fluid mixture flows, said first zone being separated from said fluid mixture to be analyzed by a first leak-tight and electrically insulating material on the top face thereof while the bottom face of said first zone is in contact with said solid electrolyte, said second zone being separated from said electrolyte on the bottom face thereof over the predetermined distance aforesaid by a second leak-tight and electrically insulating material and being adapted to communicate with said fluid mixture to be analyzed through an orifice formed in said first material.

4. A sensor according to claim 3, wherein said enclosure and said electrochemical cell are provided with a structure of revolution with respect to an axis at right angles to the plane of said first electrode, said orifice for providing a communication with the fluid mixture to be analyzed being designed in the shape of a peripheral ring and said first electrode being given a circular shape which is centered with respect to said axis of revolution.

5. A sensor according to claim 3, wherein said enclosure and said electrochemical cell are provided with a structure of revolution with respect to an axis at right angles to the plane of said first electrode, said first electrode being designed in the shape of a peripheral ring and said orifice for providing a communication with said fluid mixture being given a circular shape which is centered with respect to said axis of revolution.

6. An electrochemical sensor for measuring relative concentrations of reactive species contained in a fluid mixture, comprising:
   an electrochemical cell having a flat structure which is sensitive to an excess quantity of one of the reactive species with respect to stoichiometry of the reaction; and
   an enclosure which communicates with the fluid mixture to be analyzed at a first end and with said electrochemical cell at a second end, wherein said cell comprises:
      a first electrode in contact with said enclosure,
      a second electrode isolated from said enclosure and in contact with a reference medium, and
      a solid electrolyte which is an ionic conductor for the species to be analyzed or for an ion which is capable of reacting with said species,
   said electrolyte being in contact with said two electrodes of the electrochemical cell,
   said enclosure being designed in the form of a duct of a predetermined length and of small thickness which is parallel along its greatest dimension to the plane of said first electrode of the electrochemical cell, and
   wherein said first electrode is formed of catalytic material,
   said catalytic material also filling said duct in order to extend said first electrode in said duct and to constitute two zones such that the first zone constitutes with said second electrode and said solid electrolyte of the electrochemical cell a measurement zone which is sensitive to the species to be analyzed while the second zone extends over said predetermined length of said duct in the direction of the aforesaid first end for providing a communication with said fluid mixture to be analyzed and constitutes a zone for catalysis of said mixture, which flows through said catalytic material;
   said first zone and said second zone being further separated from said fluid mixture to be analyzed by a first leak-tight and electrically insulating material on the top face thereof while the bottom face of said first zone is in contact with said solid electrolyte,
   said second zone being further separated from said electrolyte on the bottom face thereof over said predetermined length aforesaid by a second leak-tight and electrically insulating material and being adapted to communicate with said fluid mixture to be analyzed through an orifice formed in said first material at the level of said first end.

7. A sensor according to claim 6, wherein said enclosure and said electrochemical cells are provided with a structure of revolution with respect to an axis at right angles to the plane of said first electrode, said orifice in said first leak-tight and electrically insulating material for providing a communication with the fluid mixture to be analyzed being designed in the shape of a peripheral ring and said first electrode being given a circular shape which is centered with respect to said axis of revolution.

8. A sensor according to claim 6, wherein said enclosure and said electrochemical cell are provided with a structure of revolution with respect to an axis at right angles to the plane of said first electrode, said first electrode being in the shape of a peripheral ring and said orifice in said first leak-tight and electrically insulating material for providing a communication with said fluid mixture being given a circular shape which is centered with respect to said axis of revolution.

9. A sensor according to claim 6, wherein said electrodes of said electrochemical cell and said leak-tight and electrically insulating materials are fabricated by means of the thin-film or thick-film deposition technique.

* * * * *